US011555004B2

(12) United States Patent
Zuhse et al.

(10) Patent No.: US 11,555,004 B2
(45) Date of Patent: Jan. 17, 2023

(54) METHOD FOR THE PREPARATION OF CANNABIDIOL

(71) Applicant: CHIRACON GMBH, Luckenwalde (DE)

(72) Inventors: Ralf Zuhse, Berlin (DE); Dmytro Ostrovskyi, Berlin (DE)

(73) Assignee: CHIRACON GmbH, Luckenwalde (DE)

( * ) Notice: Subject to any disclaimer, the term of this patent is extended or adjusted under 35 U.S.C. 154(b) by 0 days.

(21) Appl. No.: 17/432,696

(22) PCT Filed: Feb. 3, 2020

(86) PCT No.: PCT/DE2020/000015
§ 371 (c)(1),
(2) Date: Aug. 20, 2021

(87) PCT Pub. No.: WO2020/169135
PCT Pub. Date: Aug. 27, 2020

(65) Prior Publication Data
US 2022/0144736 A1  May 12, 2022

(30) Foreign Application Priority Data
Feb. 22, 2019 (DE) ................... 10 2019 104 563.0

(51) Int. Cl.
*C07C 37/11* (2006.01)
*C07C 37/055* (2006.01)
*C07C 37/14* (2006.01)

(52) U.S. Cl.
CPC ............ *C07C 37/055* (2013.01); *C07C 37/11* (2013.01); *C07C 37/14* (2013.01)

(58) Field of Classification Search
None
See application file for complete search history.

(56) References Cited

U.S. PATENT DOCUMENTS

| 2017/0008868 A1 | 1/2017 | Dialer et al. |
| 2019/0023680 A1 | 1/2019 | Leahy et al. |

FOREIGN PATENT DOCUMENTS

| WO | WO 2017011210 A1 | 1/2017 |
| WO | WO 2018096504 A1 | 5/2018 |
| WO | WO 2019033168 A1 | 2/2019 |

OTHER PUBLICATIONS

McClanahan, R. H. et al. "Biotransformation of Olivetol by Syncephalastrum Racemosum" J. Nat. Products vol. 47, No. 5, pp. 828-834, Sep.-Oct. 1984 (Year: 1984).*
Larson, G. L. "Silicon-Based Blocking Agents" Dec. 2015, pp. 97-126 (Year: 2015).*
PCT Notification of Transmittal of Translation of the International Preliminary Report on Patentability—Chapter II for PCT/DE2020/000015.
Translation in English—PCT/DE2020/000015—PCT International Preliminary Report on Patentability—Chapter II.
Shultz, Zachary P/ [et al.]: Enantioselective total synthesis of cannabinoids—a route for analogue development. In: Organic letters, vol. 20, 2018, No. 2, S 381-384.—ISSN 1523-7052.
Kinney, William A. [et al.]: Discovery of KLS-13019, a cannabidiol-derived neuroprotective agent, with improved potency, safety, and permeability. In: ACS Medicinal Chemstry Letters, vol. 7, 2016, No. 4, S. 424-428.—ISSN 1948-5875.
Byard, Stephen J. [et al.]: The preparation of [pentane-5,5,5-3 H 3]-abnormal-cannabidiol. In: Journal of Labelled Compounds and Radiopharmaceuticals, vol. 54, 2011, No. 4, S. 180-184.—ISSN 0362-4803.
Kobayashi, Yuichi; Takeuchi, Akira; Wang, Yong-Gang: Synthesis of cannabidiols via alkenylation of cyclohexenyl monoacetate. In: Organic Letters, vol. 8, 2006, No. 13, S. 2699-2702.—ISSN 1523-7060.
Papahatjis, Demetris P. [et al.]: Novel 1', 1' chain substituted b, 8 tetrahydrocannabinols. In: Bioorganic & Medicinal Chemistry Letters, vol. 12, 2002, No. 24, S. 3583-3586.—ISSN 0960-894X.
Vaillancourt, Valerie; Albizati, Kim F.: A one-step method for the a-arylation of camphor. Synthesis of (−)-cannabidiol and (−)-cannabidiol dimethyl ether. In: Journal of Organic Chemistry, vol. 57, 1992,No. 13, pp. 3627-3631—ISSN 0022-3263.
Crombie, Leslie [et al.]: Acid-catalysed terpenylations of olivetol in the synthesis of cannabinoids. In: Jounral of the Chemical Society, Perkin Transactions 1: Organic and Bio-Organic Chemistry, 1988, No. 5, pp. 1243-1250.—ISSN 0300-922X.
Baek, Seung-Hwa; Srebnik, Morris; Mechoulam, Raphael: Boron trifloruide etherate on alimina—a modified Lewis acid reagent. An improved synthesis of cannabidiol. In Tetrahedron Letters, vol. 26, 1985, No. 8, pp. 1083-1086.—ISSN 0040-4039.
Jung, Byumghyuck [et al.]: Synthetic strategies for (−)-Cannabidiol and its structural analogs. In: Chemistry—an Asian Journal, vol. 14, 2019, No. 21, pp. 3749-3762. _ISSN 1861-4728.
International Preliminary Examination Report—German.
International Preliminary Examination Report—English.
International Search Report.

* cited by examiner

*Primary Examiner* — Medhanit W Bahta
(74) *Attorney, Agent, or Firm* — Ralph E. Jocke; Walker & Jocke

(57) ABSTRACT

The invention relates to a method for the preparation of cannabidiol and an intermediate for the preparation of cannabidiol, wherein two intermediates are obtained, namely a silylated olivetol and a silylated olivetol (2) and brominated olivetol (4) which are stable, storable and which do not have undesirable properties or byproducts.

14 Claims, No Drawings

METHOD FOR THE PREPARATION OF CANNABIDIOL

TECHNICAL FIELD

Exemplary arrangements relate to a method for the preparation of cannabidiol and an intermediate for the preparation of cannabidiol, wherein two intermediates are obtained, namely a silylated olivetol and a silylated and brominated olivetol which are stable, storable and which do not have undesirable properties or byproducts.

BACKGROUND

For the production of drugs based on a chiral active ingredient, it is important to prepare them as enantiomerically pure as possible during synthesis. Since different enantiomers of a chiral active ingredient can have very different pharmacological effects, even slight contamination of the chiral active ingredient with the undesirable enantiomer can lead to very significant side effects in the patient that are no longer acceptable, even with a strict indication. Since a pharmacological catastrophe in the 1960s, when an active ingredient known as thalidomide was administered to pregnant women, it has been known that different enantiomers of the otherwise same substance can have very different effects. Research into this catastrophe revealed that the desired sedative effect is attributed to the (+)-(R)-enantiomer, but the teratogenic effect is attributed to the (−)-(S)-enantiomer. The peculiarity of this active ingredient is that both enantiomers convert into each other during metabolism within about eight hours by racemizing. Other chiral drugs that are metabolized in the body without prior racemization can also show very different efficacy profiles.

For the production of chiral active ingredients, different synthesis strategies are therefore pursued in order to obtain enantiomerically pure active ingredients. Three main routes are being pursued.

A first route starts from an enantiomerically pure chiral substance from which the desired molecule is synthesized. This synthesis route requires synthesis routes that suppress or at least do not promote racemization of an intermediate desired in the synthesis strategy. During synthesis, the one chiral center or even the chiral centers are no longer changed or converted by an enantioselective step. The control of such synthesis strategies is often not easy and necessary intermediate steps may cause the chiral center to racemize.

A second route to enantiomerically pure synthesis is through the preparation of the racemate, in which the racemate is separated into its enantiomers by the use of chiral auxiliaries. Chiral auxiliaries may include chromatographic methods in which the stationary phases of the chromatographic column are themselves enantiomerically pure and consist, for example, of biologically derived material. Methods which follow this synthesis strategy accept a yield of less than 50% from the outset, because at least 50% is lost as an enantiomer of a substance. If the undesired enantiomer can be racemized by using conditions more extreme than those used in the synthesis, the pure enantiomer could be obtained by continuous separation of the desired enantiomer from an always newly racemized waste product of the enantiomer separation. As a rule, such a route is economically very expensive, because the separation and racemization of a product in the cycle can be obtained with ever lower yields per cycle. Even if the racemate is recycled, one has to rely on very substantial use of chiral auxiliaries, which usually require economically significant economic resources.

Finally, a third route leads to the use of enzymes of biological origin, which generate the desired enantiomerically pure product from a prochiral intermediate by enantioselective conversion. Provided that the selected enzyme can be used at a site where the new, enantiomeric product is formed from a prochiral center of the intermediate with high selectivity, this route is often a preferred synthesis route. In fact, however, not every synthesis strategy is suitable for the use of known enzymes. A further complication, which is not uncommon, is that the prochiral center is reactive for the use of the enzyme and can therefore react spontaneously, i.e. without enzymatic catalysis, and racemize in the method. The racemic product is thus entrained past the enzymatic catalysis into the final product, where it detracts from the desired enantiomeric excess (ee).

A newer pharmacological agent, that is chiral, is cannabidiol (CBD). Cannabidiol is a barely psychoactive cannabinoid from the female hemp. Medicinally, it has anticonvulsant, anti-inflammatory, anti-anxiety, and anti-nausea effects. Other pharmacological effects, such as an antipsychotic effect, are being researched at the time of this application. Since CBD is believed to exert a variety of desirable effects in the human body when administered appropriately, efforts are being made to produce CBD synthetically whenever possible to keep it impurity-free.

In international patent application WO 2017011210 A1, a method for the preparation of dibromoolivetol is taught. However, dibromoolivetol In the method taught there, bromination with elemental bromine is carried out at low temperature. Both the handling of elemental bromine and the performance of the reaction at low temperature make the method not only unsafe to handle, but also still quite expensive in transferring the production method to the pilot plant scale or even larger scale.

SUMMARY

It is therefore a task of the exemplary arrangements to provide a method for the production of cannabidiol which is safe to handle and easier to scale up than is possible in the prior art.

The method according to the exemplary methods is characterized by silylation of the hydroxy group of the olivetol used as starting material and masking of its para position in the aromatic system. This leaves only a single coupling opportunity for further reaction with menthadienol, which makes the synthesis safe to handle and specific, and that the reaction can be carried out at room temperature. This allows the synthesis to be scaled up.

The synthesis according to the exemplary arrangements is explained in detail by the following detailed description.

DETAILED DESCRIPTION

1. Synthesis of di-OTBS Olivetol

In the exemplary arrangement the first synthesis step for the preparation of cannabidiol is performed by silylating olivetol with TBSCl (tert-butyldimethylsilyl chloride).

In this case, the olivetol may be substituted on the pentyl chain at the positions of R with one or more substituents consisting of hydrogen (H), deuterium (D) or tritium (T), alkoxy, such as methoxy ($—OCH_3$), ethoxy ($—OC_2H_5$), nitro ($—NO_2$), fluorine (—F), chlorine (—Cl), bromine (—Br), alkyl from methyl, ethyl, propyl to butyl.

The first synthesis step is described using the unsubstituted olivetol (R=H).

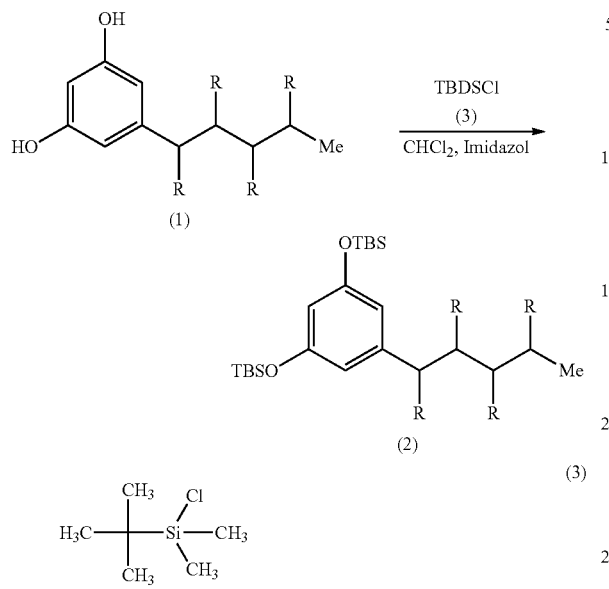

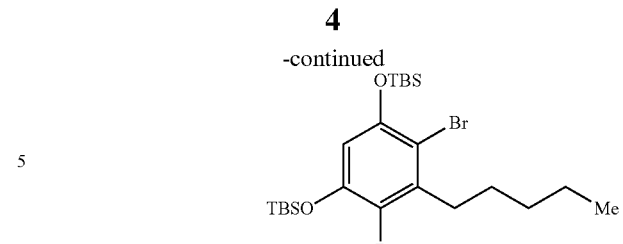

4.0108 g olivetol (5-pentylresorcinol) (1) and 3.6330 g imidazole (2.4 equivalents) (1,3-diaza-2,4-cyclopentadiene) are dissolved in 48 ml dichloromethane (CH$_2$Cl$_2$), and 7.7864 g TBSCl (tert-butyldimethylsilyl chloride) (3) are added to the obtained solution in portions.

The resulting suspension is stirred at room temperature for 16 hours. Then 30 ml of deionized water (deionized water, fully demineralized water) is added. An emulsion is formed, the solid of which is dissolved in the aqueous phase. The emulsion is stirred for at least 30 minutes at room temperature. The phases are separated after the specified time. The aqueous phase is extracted twice with 40 ml of dichloromethane (CH$_2$Cl$_2$). The combined organic phases are washed with 40 ml deionized water and dried with sodium sulfate (NaSO$_4$). The resulting suspension is aspirated through a filter frit, and the solid is washed with 15 ml dichloromethane (CH$_2$Cl$_2$).

The filtrate is then concentrated at a bath temperature of 40° C. to a final pressure of 12 mbar. 9.2158 g of final product can be isolated (100% yield=9.0964 g).

The 3,5-di-(di-O-tert-butyldimethylsilyl)-5-pentylresorcinol (2) thus obtained is stable, storable and transportable, and is suitable as a marketable reactant for the preparation of optionally substituted cannabidiols.

The product, di-O-tert-butyldimethylsilyl-5-pentylresorcinol (2), is further reacted without further purification.

2. Synthesis of di-OTBS-dibromolivetol

The exemplary second synthesis step is carried out by brominating the di-O-tert-butyldimethylsilyl-5-pentylresorcinol (2) obtained in the previous step.

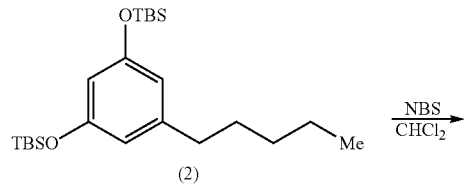

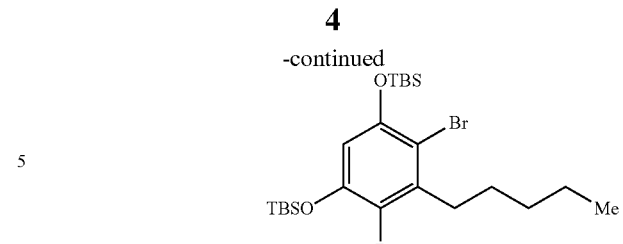

Dissolve 9.2158 g crude di-OTBS olivetol (di-O-tert-butyldimethylsilyl-5-pentylresorcinol) (2) in 90 ml dichloromethane (CH$_2$Cl$_2$). The obtained solution is cooled to 0° C. 8.7126 g of N-bromosuccinimide (NBS, 2.2 equivalents) (5) is added in portions with stirring. External cooling is then removed and the resulting suspension is heated until room temperature is reached. Added NBS dissolves slowly over time. After 2 hours 5 minutes a clear solution is formed. Finally, a fine white solid precipitates after an additional 15 minutes of stirring. A reaction check by thin layer chromatography (TLC) shows that almost 100% conversion takes place. The suspension is stirred for a further 17 hours. The suspension is then aspirated through a filter frit, and the filter cake is washed with 10 ml of dichloromethane (CH$_2$Cl$_2$). The filtrate obtained is then concentrated on a rotary evaporator at a bath temperature of 40° C. A mixture of an oil and solid is obtained. To the mixture, 50 ml of cyclohexane (C$_6$H$_{12}$) is added and stirred briefly at room temperature. The residue of NBS is filtered off and the filtrate is concentrated on a rotary evaporator at a bath temperature of 40° C. to a final pressure of 13 mbar. 12.2000 g of final product was isolated (yield=96.8%).

$^1$H NMR spectrum shows only the appearance of traces of TBSCl as the only impurity.

The di-OTBS-dibromolivetol (4,6-dibromo-di-O-tert-butyldimethylsilyl-5-pentylresorcinol) (4) thus obtained is stable, storable and transportable and is suitable as a marketable reactant for the preparation of optionally substituted cannabidiols.

3. Synthesis of Dibromolivetol

In the exemplary third synthesis step, the di-OTBS-dibromolivetol (4,6-dibromo-di-O-tert-butyldimethylsilyl-5-pentylresorcinol) (4) obtained in the previous step is desilylated.

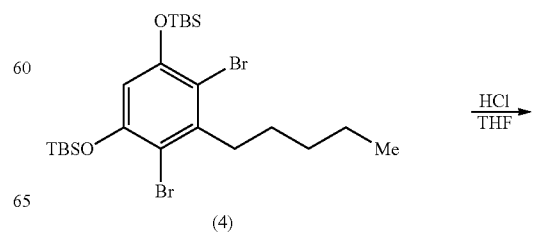

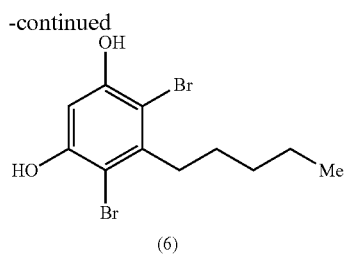

(6)

(7)

Dissolve 25.23 g of di-OTBS-dibromolivetol (4,6-dibromo-di-O-tert-butyldimethylsilyl-5-pentylresorcinol) (4) in 150 ml of tetrahydrofuran ($C_4H_8O$) and add 11 ml of deionized water and 46 ml of 25% hydrochloric acid with stirring. A biphasic emulsion is formed. The emulsion is stirred at room temperature until a clear solution is formed. Reaction control by thin layer chromatography shows 100% conversion after 71 hours. 77 ml of 15% sodium hydroxide solution is added dropwise over 20 minutes until the pH value of 2 to 3 is reached. A biphasic emulsion is formed. The phases are separated and the aqueous phase is extracted twice with 150 ml tert-butyl methyl ether. The combined organic phases are washed with 100 ml of saline solution and dried with sodium sulfate. The resulting suspension is aspirated through a filter frit, and the filter cake is washed twice with 20 ml of tert-butyl methyl ether. The filtrate is concentrated on a rotary evaporator at a bath temperature of 40° C. to a final pressure of 18 mbar. The crude product obtained is dissolved in 60 ml of cyclohexane. 1.2 ml deionized water is added dropwise to the cyclohexane solution with stirring. A precipitate is formed. The suspension is cooled until the internal temperature reaches the value of 5 to 10° C. The cooled mixture is stirred for a further 10 minutes. The solid is aspirated, washed twice with 10 ml of cyclohexane and dried in air at room temperature. 8.5352 g of final product can be isolated (yield=57%).

$^1$H NMR spectrum shows that no impurities are present.

4. Synthesis of Dibromocannabidiol

In the exemplary fourth synthesis step, the dibromolivetol (4,6-dibromo-5-pentylresorcinol) (6) obtained in the previous step is converted into dibromocannabidiol (9) by reaction with trans-menthadienol (4R-isopropenyl-1-methylcyclohex-2-enol) (8).

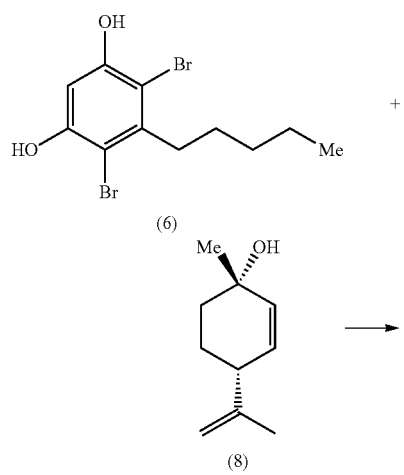

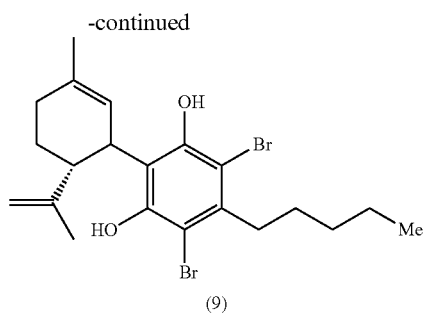

(9)

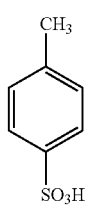

(7)

3.4028 g dibromolivetol (4,6-dibromo-5-pentylresorcinol) (6) is dissolved in 51 ml dichloromethane ($CH_2Cl_2$). The obtained solution is concentrated on a rotary evaporator at a bath temperature of 40° C. to a final pressure of 15 mbar. The obtained oil solidifies rapidly during cooling.

The solid is mixed with 3.5323 g magnesium sulfate (MgSO4) and 0.9614 g para-toluenesulfonic acid-monohydrate (pTSA, 0.5 equivalent) (7). Then 25 ml of dichloromethane (CH2Cl2) is added to the mixture. A suspension is formed. The suspension is cooled to a temperature of −20° C. to −10° C. in an ethanol/nitrogen bath.

2.1432 g of trans-menthadienol (4R-isopropenyl-1-methylcyclohex-2-enol) (1.4 equivalents) (8) is dissolved in 9 ml of dichloromethane (CH2Cl2) and the resulting solution is added to the reaction mixture dropwise over 12 minutes. The reaction mixture is stirred for 5 hours and then stored in a freezer at T=−25° C. overnight. The mixture is then mixed with 10 ml sodium hydrogen carbonate solution without heating. The resulting emulsion is warmed to room temperature and diluted with 20 ml deionized water. The phases are separated. The aqueous phase is extracted twice with 50 ml dichloromethane ($CH_2Cl_2$). The combined organic phases are washed with 30 ml of saline solution and dried with sodium sulfate ($Na_2SO_4$). The resulting suspension is aspirated through a filter frit. The filter cake is washed three times with 10 ml dichloromethane (CH2Cl2) and the filtrate is concentrated on a rotary evaporator at a bath temperature of 40° C. to a final pressure of 12 mbar. 5.2315 g of crude product is obtained. To the crude product is added 10 ml of cyclohexane ($C_6H_{12}$). A solution is obtained. The solution is cooled to an internal temperature of 5 to 10° C. and 0.04 ml deionized water is added with stirring. A precipitate forms at the edge of the flask. The resulting suspension is stirred for an additional 25 minutes and the solid is filtered off and washed with 3 ml of cyclohexane ($C_6H_{12}$). The filtrate is concentrated on a rotary evaporator at a bath temperature of 40° C. to a final pressure of 12 mbar. 4.7400 g of target product can be isolated.

$^1$H NMR spectrum shows approximately 85% purity.

5. Synthesis of Cannabidiol (CBD)

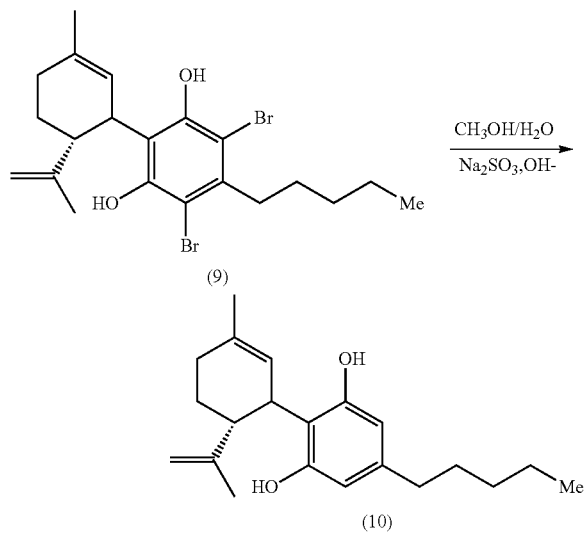 [SMILES: C=C(C)[C@@H]1CCC(C)=CC1c1c(O)c(Br)c(CCCCC)c(Br)c1O ; C=C(C)[C@@H]1CCC(C)=CC1c1c(O)cc(CCCCC)cc1O]

4.74 g crude dibromocannabidiol (9) is mixed with 47 ml methanol (CH$_3$OH). A very thin suspension is obtained. 7.5912 g sodium sulfite (Na$_2$SO$_3$) (6 equivalents) are dissolved in 50 ml deionized water and the solution is added to the reaction mixture. A white precipitate is formed. 3 ml of 25% ammonia solution (approx. 4 equivalents) is added to the reaction mixture after 30 minutes with stirring.

Reaction control by thin layer chromatography (TLC) shows no final product in the mixture and appearance of a monobromo derivative after 19 hours of stirring.

Additional 0.75 ml ammonia solution (NH$_3$/H$_2$O) is added and the suspension is heated to T=60° C. After 19 hours DC shows 100% conversion of starting substance and traces of CBD.

2.07 ml of triethylamine (C$_2$H$_5$)$_3$N (1.5 equivalent) is added and the suspension is stirred for 40 hours. DC shows CBD as the main product with traces of the monobromo derivative.

The mixture is cooled to room temperature. 4.2 ml acetic acid (approx. 7.2 equivalents) is added dropwise (until pH is in the range of 6-7). The mixture is diluted with 40 ml methanol and aspirated through a filter frit. The filter cake is washed with 20 ml methanol. The filtrate is extracted three times with 150 ml of n-heptane. The combined n-heptane fractions are washed with 100 ml deionized water and dried with sodium sulfate. The resulting suspension is aspirated through a filter frit, and solids are washed with 30 ml of n-heptane. The light-yellow filtrate on the rotary evaporator is concentrated at a bath temperature of 40° C. to a final pressure of 20 mbar. The residue obtained is recrystallized from 2 ml of n-heptane. Mass of the final product=649.3 mg (total yield after 2 steps=20%).

Diisopropyl-ethylamine (C$_8$H$_{19}$)$_3$N, triethylamine (C$_2$H$_5$)$_3$N and/or diazabicycloundecene (DBU, C$_9$H$_{16}$N$_2$) are suitable additional bases for debromination.

Analytical Data:
$^1$H-NMR (CDCl3): δ=0.88 (t, 3H, J=7.0 Hz), 1.29 (m, 4H), 1.55 (m, 2H), 1.66 (s, 3H), 1.79 (s, 3H), 1.82 (m, 2H), 2.08 (m, 1H), 2.23 (m, 1H), 2.42 (m, 3H), 3.85 (m, 1H), 4.56 (s, 1H), 4.66 (br. s, 2H), 5.57 (d, 1H, J=1.2 Hz), 5.98 (br. s., 1H), 6.16 (br. s., 1H), 6.28 (br. s., 1H).

HPLC: 99, 8% purity. [α]$_D$=−130.6° (c=0.49 in ethanol).

The occurrence of stereoisomers cannot be detected by NMR and HPLC.

REFERENCE LIST

1. Olivetol (5-pentylresorcinol)
2. Di-OTBS olivetol (di-O-tert-butyldimethylsilyl-5-pentyl-resorcinol)
3. TBSCl (tert-butyldimethylsilyl chloride)
4. Di-OTBS-dibromolivetol (4,6-dibromo-di-O-tert-butyldimethylsilyl-5-pentylresorcinol)
5. N-bromosuccinimide
6. Dibromolivetol (4,6-dibromo-5-pentylresorcinol)
7. pTSA (para-toluenesulfonic acid monohydrate
8. trans-menthadienol (4R-isopropenyl-1-methylcyclohex-2-enol)
9. Dibromocannabidiol
10. Cannabidiol (2-[(1R,6R)-3-Methyl-6-prop-1-en-2-yl-1-cyclohex-2-enyl]-5-pentylbenzo-1,3-diol)

The invention claimed is:
1. A method for the preparation of cannabidiol (10) (2-[(1R,6R)-3-methyl-6-prop-1-en-2-yl-1-cyclohex-2-enyl]-5-pentylbenzo-1,3-diol) or its pentyl-substituted derivatives, comprising the steps of:
   a) silylating olivetol (5-pentylresorcinol) (1) substituted or unsubstituted at the pentyl chain with TBSCl (tert-butyldimethylsilyl chloride) (3), according to the following reaction scheme:

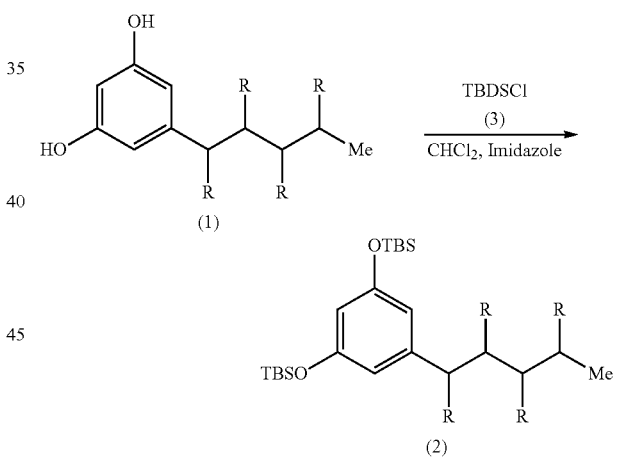

wherein the pentyl substituents R are substituted with substituents selected from the group consisting of:
hydrogen (H), alkoxy, nitro (—NO$_2$), fluorine (—F), chlorine (—Cl), bromine (—Br), and alkyl, wherein the alkyl is selected from methyl, ethyl, propyl or butyl,
giving a corresponding unsubstituted (R=H) or substituted di-O-tert-butyldimethylsilyl-5-pentylresorcinol (2),
   b) brominating the di-O-tert-butyldimethylsilyl-5-pentylresorcinol (2) obtained in the first step and optionally substituted to di-OTBS-dibromolivetol (4,6-dibromo-di-O-tert-butyldimethylsilyl-5-pentylresorcinol),
   c) desilylating the di-OTBS-dibromolivetol (4,6-dibromo-di-O-tert-butyldimethylsilyl-5-pentylresorcinol) obtained in the previous step and optionally substituted to dibromolivetol (4,6-dibromo-5-pentylresorcinol) or the corresponding substituted derivative, d) reacting the dibromolivetol (4,6-dibromo-5-pentylresorcinol) or the corresponding substituted derivative obtained in the previous step with trans-menthadienol (4R-isopropenyl-1-methylcyclohex-2-enol) (8) to give dibromocannabidiol (9) or its corresponding substituted derivative, e) debrominating the dibromocannabidiol (9) obtained in the previous step or its corresponding substituted derivative to cannabidiol or its corresponding derivative.

2. The method according to claim 1, wherein (b) includes a bromination with N-bromosuccinimide in dichloromethane ($CH_2Cl_2$).

3. The method according to claim 2, wherein (c) includes desilyation by acid hydrolysis in tetrahydrofaun.

4. The method according to claim 2, further comprising the step of:
conversion to dibromocannabidiol in dichloromethane ($CH_2Cl_2$) in the presence of paratoluenesulfonic acid.

5. The method according to claim 2, wherein (e) includes debromination of the dibromoicannabidiol in methanol in the presence of at least one base selected from the group consisting of ammonia ($NH_3$), diisopropyl ethlyamine ($C_8H_{19})_3N$, triethylamine ($C_2H_5)_3N$ and/or diazabicycloundecene (DBU, $C_9H_{16}N_2$).

6. The method according to claim 1, wherein (c) includes desilylation by acid hydrolysis in tetrahydrofuran.

7. The method according to claim 6, and further comprising:
conversion to dibromocannabidiol in dichloromethane ($CH_2Cl_2$) in the presence of para-toluenesulfonic acid.

8. The method according to claim 6, wherein (e) includes debromination of the dibromoicannabidiol in methanol in the presence of at least one base selected from the group consisting of ammonia ($NH_3$), diisopropyl ethlyamine ($C_8H_{19})_3N$, triethylamine ($C_2H_5)_3N$ and/or diazabicycloundecene (DBU, $C_9H_{16}N_2$).

9. The method according to claim 1, and further comprising:
conversion to dibromocannabidiol in dichloromethane ($CH_2Cl_2$) in the presence of para-toluenesulfonic acid.

10. The method according to claim 9, wherein (e) includes debromination of the dibromoicannabidiol in methanol in the presence of at least one base selected from the group consisting of ammonia ($NH_3$), diisopropyl ethlyamine ($C_8H_{19})_3N$, triethylamine ($C_2H_5)_3N$ and/or diazabicycloundecene (DBU, $C_9H_{16}N_2$).

11. The method according to claim 1, wherein (e) includes debromination of the dibromoicannabidiol in methanol in the presence of at least one base selected from the group consisting of ammonia ($NH_3$), diisopropyl ethlyamine ($C_8H_{19})_3N$, triethylamine ($C_2H_5)_3N$ and/or diazabicycloundecene (DBU, $C_9H_{16}N_2$).

12. The method according to claim 1, wherein the alkoxy is methoxy (—$OCH_3$) or ethoxy (—$OC_2H_5$).

13. A composition of matter, comprising:
silylated and brominated olivetol with the following structure

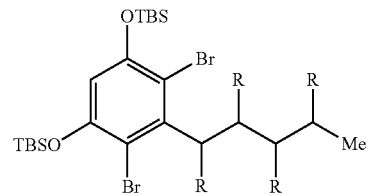

with
OTBS O-tert-butyldimethylsilyl, and
wherein each radical R is selected from the group consisting of hydrogen (H) alkoxy, nitro (—$NO_2$), fluorine (—F), chlorine (—Cl), bromine (—Br), and alkyl, wherein the alkyl is selected from methyl, ethyl, propyl or butyl.

14. The method according to claim 13, wherein the alkoxy is methoxy (—$OCH_3$) or ethoxy (—$OC_2H_5$).

* * * * *